(12) United States Patent
Xing et al.

(10) Patent No.: US 9,861,834 B2
(45) Date of Patent: Jan. 9, 2018

(54) STATION PARAMETER OPTIMIZED RADIATION THERAPY (SPORT): A NOVEL SCHEME FOR TREATMENT PLANNING AND DELIVERY IN RADIATION THERAPY

(71) Applicant: The Board of Trustees of the Leland Stanford Junior University, Palo Alto, CA (US)

(72) Inventors: Lei Xing, Palo Alto, CA (US); Ruijiang Li, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 434 days.

(21) Appl. No.: 14/268,290

(22) Filed: May 2, 2014

(65) Prior Publication Data

US 2014/0330064 A1 Nov. 6, 2014

Related U.S. Application Data

(60) Provisional application No. 61/818,669, filed on May 2, 2013.

(51) Int. Cl.
*A61N 5/10* (2006.01)

(52) U.S. Cl.
CPC ......... *A61N 5/1031* (2013.01); *A61N 5/1047* (2013.01)

(58) Field of Classification Search
CPC ... A61N 5/1031; A61N 5/1047; A61N 5/1042
See application file for complete search history.

(56) References Cited

U.S. PATENT DOCUMENTS

2013/0131428 A1* 5/2013 Jiang .................... A61N 5/1031
600/1

* cited by examiner

*Primary Examiner* — Christine H Matthews
(74) *Attorney, Agent, or Firm* — Lumen Patent Firm

(57) ABSTRACT

A method of radiation therapy planning and delivery is provided that includes introducing a demand metric, using a volumetric modulation arc therapy system, to select a spatially optimized and non-uniform set of station or control points to be used for intensity modulation, where the set of station or control points are uniform or non-uniform, and selecting a set of control points at different gantry angles, using the volumetric modulated arc therapy system, and using the demand metric to prioritize which station or control point receives intensity modulation, where the volumetric modulated arc therapy system is differentially boosted at selected angles by inserting additional segments to the station, where the inserted additional apertures dosimetrically boost desired regions in a planning target volume to improve planning target volume coverage in a single arc rotation while sparing sensitive structures.

7 Claims, 2 Drawing Sheets

(a)   Prior Art (b)

STATION PARAMETER OPTIMIZED RADIATION THERAPY (SPORT): A NOVEL SCHEME FOR TREATMENT PLANNING AND DELIVERY IN RADIATION THERAPY

CROSS-REFERENCE TO RELATED APPLICATIONS

This application claims priority from U.S. Provisional Patent Application 61/818,669 filed May 2, 2013, which is incorporated herein by reference.

STATEMENT OF GOVERNMENT SPONSORED SUPPORT

This invention was made with Government support under grant (or contract) no. 1R01 CA133474, 1R21 CA153587 awarded by the National Institutes of Health (NIH). The Government has certain rights in this invention.

FIELD OF THE INVENTION

The present invention relates generally to radiation therapy. More particularly, the invention relates to improved radiation therapy planning and delivery using a station parameter optimized radiation therapy (SPORT) method.

BACKGROUND OF THE INVENTION

Intensity modulated radiation therapy (IMRT) and VMAT are the mostly widely used treatment planning and delivery techniques in radiation therapy. However, conventional IMRT (with 5-10 beams) often does not possess sufficient angular sampling required to spatially spread the dose. On the contrary, current VMAT (with 1-3 arcs) oversamples the angular space and does not provide the desired intra-beam intensity modulation in some or all directions. More specifically, conventional VMAT discretizes the angular space into equally spaced control points during planning and then optimizes the apertures and weights of the control points. The aperture at an angle in between two control points is obtained through interpolation. This approach tacitly ignores the differential need for intensity modulation of different angles. As such, multiple arcs are often required, which may oversample some angle(s) and undersample others.

What is needed is a method to differentially distribute the station points in the angular space according to the need of the specific case in order to best cover the target volume and spare the sensitive structures. In case of rotational arc therapy, this is to segmentally boost the VMAT scheme to eliminate the need for multiple arcs in VMAT treatment with improved dose distribution and/or delivery efficiency. More generally, what is needed is a method of radiation therapy planning and delivery that involves optimization of the fundamental system variables characterizing the station points (or control points) of a digital linear accelerator in unison, instead of optimization of the beam fluence parameters, which is typically a composite of a set of station parameters, or optimization of a pre-distributed set of beams.

SUMMARY OF THE INVENTION

A method of radiation therapy planning and delivery is provided that includes introducing a demand metric, using a volumetric modulation arc therapy system, to select a spatially optimized set of station or control points to be used for intensity modulation, where the set of station or control points are uniform or non-uniform, and selecting a set of control points at different gantry angles, using the volumetric modulated arc therapy system, and using the demand metric to prioritize which station or control point receives intensity modulation, where the volumetric modulated arc therapy system is differentially boosted at selected angles by inserting additional segments to the station, where the inserted additional apertures dosimetrically boost desired regions in a planning target volume to improve planning target volume coverage in a single arc rotation while sparing sensitive structures.

According to one aspect of the invention, a distribution of radiotherapy dose is optimized using non-uniform angular beam sampling, sparse intensity modulation, or the non-uniform angular beam sampling and the sparse intensity modulation.

According to another aspect, the spatially optimized set is selected using an on-demand selection process or a pre-selection process.

In another aspect of the invention a delivery plan, used by the volumetric modulated arc therapy system having a multi-leaf collimator, is capable of interpolating each of two adjacent apertures of the multi-leaf collimator at a control point, where when at least two apertures have a same gantry angle, the gantry rotation stops at a gantry angle and delivers radiotherapy doses to each aperture one by one, where no radiotherapy dose is applied when the aperture is transitioning to the next the aperture at the same gantry angle.

In a further aspect of the invention, a delivery plan, used by the volumetric modulated arc therapy system, is capable of re-optimizing the segment shape and weight of a the station or the control point.

In yet another aspect of the invention, a delivery plan, used by the volumetric modulated arc therapy system, includes a step-and-shoot delivery operation or a continuous arc delivery operation.

According to one embodiment, the invention is a method of radiation therapy planning and delivery that includes pre-selecting or optimizing a number of station or control points, using a volumetric modulation arc therapy system, and optimizing the shape or weight of a field corresponding to each the control point simultaneously with the spatial distribution of the control points, using the volumetric modulation arc therapy system.

DETAILED DESCRIPTION

Figure 1:
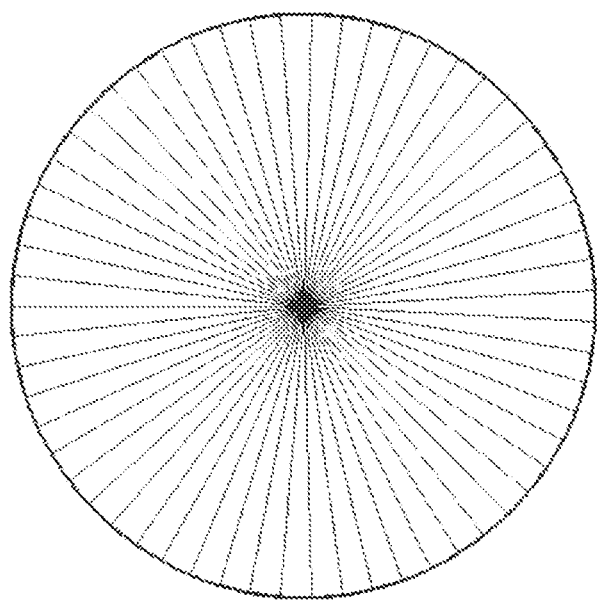
FIGS. 1a-1b show schematic drawings of the beam angular distributions of VMAT (1a) and SPORT (1b), according to one embodiment of the invention.
Figure 1:
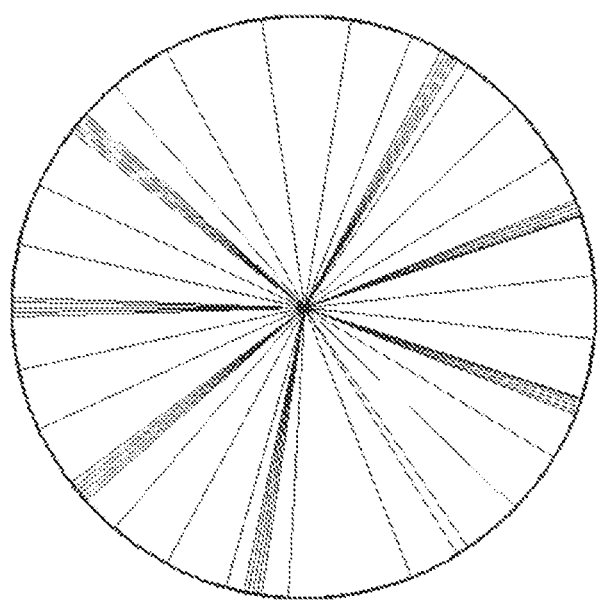

A method of radiation therapy planning and delivery is provided that involves optimization of the fundamental system variables characterizing the station points (or control points) of a digital linear accelerator in unison, instead of optimization of the beam fluence parameters, which is typically a composite of a set of station parameters, or optimization of a pre-distributed set of beams. The method, referred to as station parameter optimized radiation therapy (SPORT), can be implemented and realized in different ways depending on the clinical goal and/or predefined solution space. A realization scheme, for example, is rotational arc SPORT, which improves current volumetric arc therapy (VMAT) by using only a single arc rotation to produce a spatially optimized conformal dose distribution across a non-uniform distribution or station points. This scheme is realized by allowing differential angular distribution of the station points in accordance to the actual demand of the specific clinical case. For example, a rotational arc SPORT plan can be obtained by introducing a demand metric, using a volumetric modulation arc therapy system, to select a station or a control point to be used for dose delivery, and applying an on-demand metric or pre-selection process or other optimization methods, using the volumetric modulated arc therapy system, to select a set of the control points at different gantry angles, where the demand metric prioritizes which station or control point receives intensity modulation, where the volumetric modulated arc therapy system is differentially boosted at selected angles by inserting additional segments, where the inserted additional segmented arcs of the additional apertures dosimetrically boost desired regions in the planning target volume to improve planning target volume coverage in a single arc rotation while sparing sensitive structures. In general, a SPORT plan is obtained using an optimization algorithm to directly optimize the angular and spatial distribution of the station points along with their apertures and weights.

SPORT can be implemented and realized in different ways depending on the clinical goal and/or predefined solution space. A realization scheme, for example, is rotational arc SPORT, which improves current volumetric arc therapy (VMAT) by using only a single arc rotation to produce a conformal dose distribution. This method of radiation therapy planning and delivery is provided that includes introducing a demand metric, using a volumetric modulation arc therapy system, to select a station or a control point to be used for intensity modulation, and applying an on-demand metric or pre-selection process, using the volumetric modulated arc therapy system, to select a set of the stations or control points at different gantry angles, where the demand metric prioritizes which station or control point receives more (or less) intensity modulation, where the volumetric modulated arc therapy system is differentially boosted at selected angles by inserting additional segments on an on-demand basis, where the inserted additional segments dosimetrically boost desired regions in the planning target volume to improve planning target volume coverage in a single arc rotation while sparing sensitive structures.

According to one embodiment, the invention provides a method of radiation therapy (VMAT) planning and delivery that includes pre-selecting a number of station or control points, using a VMAT system and optimizing the spatial distribution of the control points simultaneously with the segment shape or weight corresponding to each control point, using the volumetric modulation arc therapy system.

In current aperture-based VMAT optimization methods, the angular space is divided into equally spaced directions (nodes or stations) and the field weights and apertures of the incident beams from these directions are then optimized using a segment based optimization algorithm. The field in between two adjacent nodes is realized by linear interpolation of the beam parameters of the two adjacent nodes. This approach is not optimal and, depending on the size of the angular discretization, some directions may be under-modulated and some may be over-modulated. In current implementations, VMAT generally does not offer sufficient beam modulation (which can be stated as the aperture and/or intensity modulation per unit angle), as evidenced by the need for two or multiple arcs for many clinically cases.

Radiation therapy is stepping into a digital era, in which treatments will be done "station by station" (or "node by node" or "control-point-by-control-point"), instead of "beam by beam". In brief, a station or a node describes the state of delivery system (including LINAC configurations such as beam energy, aperture shape and weight, gantry/collimator angle and auxiliaries such as the couch). When the auxiliary parameters are kept constant, a node or station defines nothing more than an MLC or jaw-shaped beam. A conventional intensity-modulated beam includes a collection of stations with the same gantry angle but different MLC segments.

The current invention provides a station parameter optimized radiation therapy (SPORT) method to optimize the station intensity, spatial distribution and other parameters characterizing the station. It achieves highly conformal dose distributions through optimal sampling of station points and at the same time maintains high delivery efficiency. In general, these plans have non-uniform angular station points sampling and sparse intensity modulation. There are two different approaches for the new planning and delivery scheme.

According to one aspect of the invention, a selected number of segments are boosted at certain directions. Here an arc strategy is used in which the traditional one-arc VMAT is differentially boosted at selected angle(s) by inserting additional segments on an on-demand basis. The added segments are then optimized together with the original set of station or control points as a whole. The insertions of additional apertures dosimetrically "boost" some regions in the planning target volume (PTV) to improve the PTV coverage while improving the sparing of the sensitive structures. As a result of the selective boost, the dose distribution can be dramatically improved as compared with VMAT. Importantly, the delivery of the segment-boosted plan can still be accomplished by a single rotation. The invention provides a rotational arc SPORT (i.e. a radiation therapy technique by delivering a segment-boost scheme that is planned and delivered in a single arc rotation).

The essence of the new treatment method according to the current invention is how to identify the need of individual angles for intensity modulation and to provide the necessary beam intensity modulation for those beam angles that will benefit from additional modulation. According to one embodiment, a "demand metric" is introduced at each control point to decide which station or control points need intensity modulation. To this end, the degree of segmental modulation around each station control point is examined and then more segments are placed around the control points with higher modulations, where adding segment(s) to these station control points is more beneficial for improved dose distribution. To quantify the level of intensity modulation for each station point, a modulation index (MI) is defined as follows:

$$MI(s) = \sum_{\substack{k=-K...\\K,k\neq 0}} \left[ \sum_{i=1}^{60} (|x_i^A(s) - x_i^A(s+k)| + |x_i^B(s) - x_i^B(s+k)|) \right] \cdot \left| \frac{MU(s) - MU(s+k)}{\alpha(s) - \alpha(s+k)} \right|$$

where, and $x_i^A(s)$ and $x_i^B(s)$ are the i-th MLC leaf positions at banks A and B at the s-th station control point, MU is the cumulative monitor units, $\alpha$ is the gantry angle. MI is the local geometric modulation weighted by the corresponding segmental MU per gantry angle. Thus it is a direct measure of the control point's contribution to dose distributions.

According to one embodiment of the invention, the treatment plan can be delivered by commercial medical linear accelerators, without requirement for modifications of existing system hardware.

In another embodiment, the planning scheme achieves optimal dose distributions by non-uniform angular beam sampling and/or sparse intensity modulation. This distinguishes it from VMAT with uniform angular beam sampling (thereby limiting the degrees of freedom and achievable dose distributions) and IMRT with few beams and many segments (prolonging treatment time).

Figure 2:
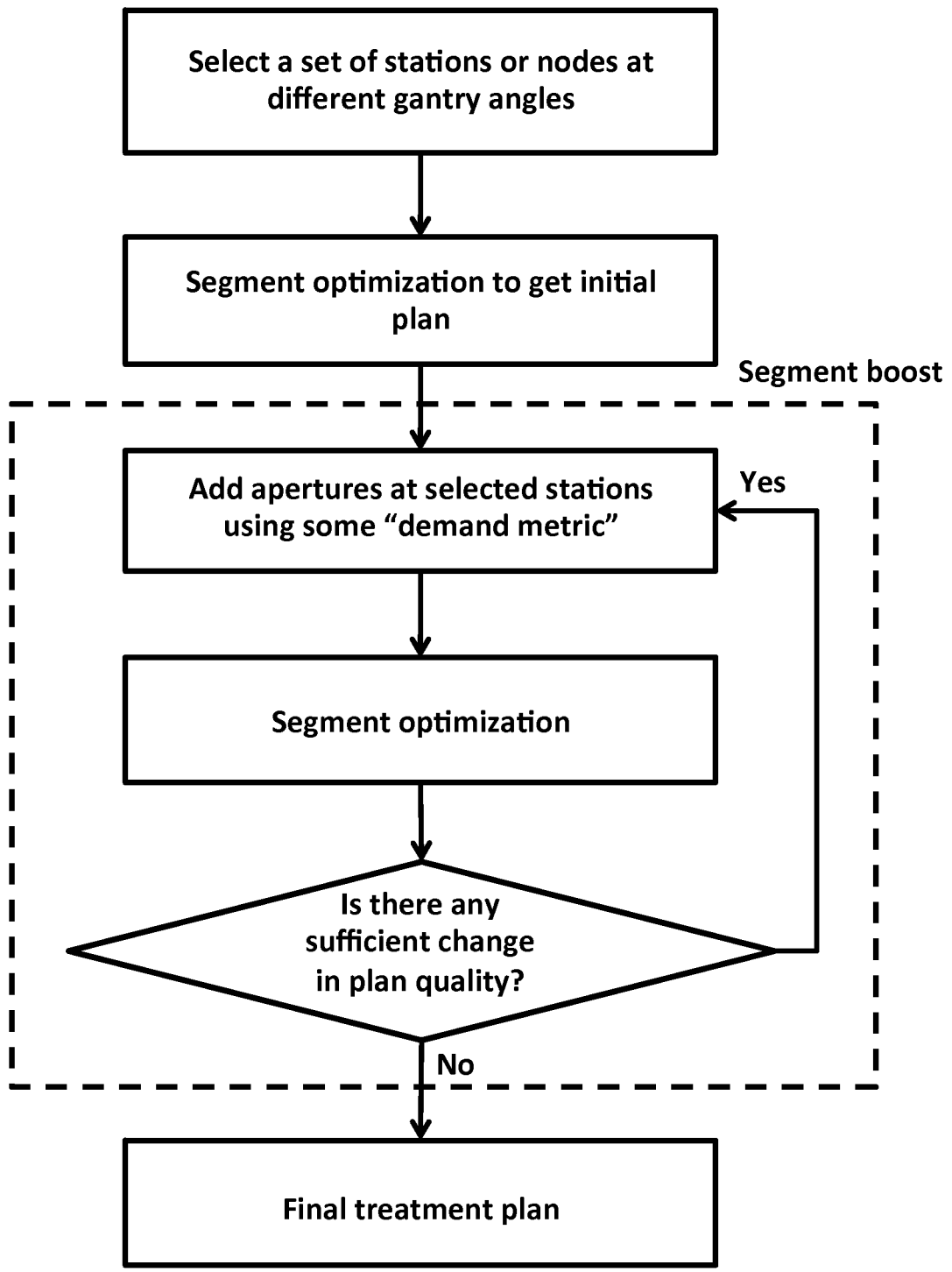
FIG. 2 shows a flow diagram of the segment boost, according to one embodiment of the invention.

Different from VMAT, the current invention does not impose a uniform angular spacing requirement between two consecutive beams. Instead, the stations are distributed nonuniformlly according to the requirement of each clinical case—some nodes can even have the same gantry angle. By allowing nonuniform nodal sampling, it addresses the need for desired beam intensity modulation in certain directions. This important feature is what sets the rotational arc SPORT apart from VMAT. FIGS. 1a-1b show schematic drawings of the beam angular distributions of VMAT (see FIG. 1a) and SPORT (see FIG. 1b). FIG. 2 shows the flowchart of the segment boost planning method. The delivery of the plan in a single arc is then realized by interpolating each of the two adjacent apertures. When two or more apertures have the same gantry angle, the gantry stops rotation at the station point and delivers the apertures one by one (except the aperture that is used to link to the next aperture at a different gantry angle).

The above planning strategy relies on the adaptive adding of new apertures to reach to the optimized single arc plan (which may or may not include multiple apertures at some gantry angles). According to a further embodiment of the invention, first obtained is a multiple-beam IMRT plan with each beam's intensity profile sparsified by using total-variation regularization. The segments of each beam are then distributed around the stations/nodes according to a certain heuristic rule to form a single arc plan. For example, a subset of the segments (or all segments) at each beam is redistributed to neighboring angles at 2° intervals, so that each new beam contains only one aperture. If there are too many segments at a beam, then most of the segments of the beam can be delivered by stopping the gantry. The segment redistribution process is optimized such that the total MLC leaf travel distance between consecutive segments is minimized. Due to the large number of beams initially selected, the angular difference for displaced segments is small (typically <5°). So the beam angular redistribution process has minimal effect on the resultant dose distributions. The segment weight and shape may be re-optimized as a final step in the treatment planning stage. For treatment delivery, in those beams with multiple segments, a step-and-shoot approach is used and in between, a continuous arc delivery is used. A new generation of digital linacs with auto-field sequencing has become commercially available, which improves dramatically the delivery efficiency.

The above planning approaches are different and yet converging techniques for realizing the proposed SPORT scheme. Both approaches aim to achieve optimal dose distributions and efficient delivery by non-uniform angular beam sampling and sparse intensity modulation.

According to a further embodiment of the invention, the new scheme achieves fast delivery by eliminating dispensable intra-beam intensity modulation using novel compressed-sensing (or other sparse data processing technique that lead to piece-wise constant fluence) strategies for dose optimization and planning. The use of a continuous arc and auto-field sequencing afforded by digital linacs further speeds up the delivery process.

Variations of the different embodiments of the current invention include both beam energy, collimator rotation and couch translation/rotation can be modulated and optimized during treatment planning. Additionally, the new scheme can incorporate more complex beam configurations such as non-coplanar and non-isocentric beams, into the treatment planning and delivery process. Also, different optimization algorithms can be implemented to realize the above two schemes.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A method of radiation therapy planning and delivery, comprising:
    a. selecting a spatially optimized distribution set of station points or control points to be used for intensity modulation using a demand metric in a volumetric modulation arc therapy system, wherein said set of spatially optimized distribution of station points or control points are non-uniform, wherein a gantry is positioned according to said selected non-uniform station points or control points; and
    b. moving said gantry and selecting a different set of said spatially optimized distribution set of station points or control points at different gantry angles, using said volumetric modulation arc therapy system, and using said demand metric to prioritize which said station point or said control point receives intensity modulation and differentially boosting said volumetric modulation arc therapy system at selected angles by using an additional state of a beam energy, state of a beam aperture, state of a beam shape, state of a beam weight, state of a gantry angle, state of a collimator angle and state of a couch position to a station, wherein said additional beam aperture state dosimetrically boosts desired regions in a planning target volume to improve planning target volume coverage in a single arc rotation while sparing sensitive structures.

2. The method of radiation therapy planning and delivery of claim 1, wherein a distribution of radiotherapy dose is optimized using non-uniform angular beam sampling, sparse intensity modulation, or said non-uniform angular beam sampling and said sparse intensity modulation.

3. The method of radiation therapy planning and delivery of claim 1, wherein said spatially optimized set is selected using an on-demand selection process or a pre-selection process.

4. The method of radiation therapy planning and delivery of claim 1, wherein a delivery plan, used by said volumetric modulation arc therapy system which further comprises a multi-leaf collimator, is capable of interpolating each of two adjacent apertures of said multi-leaf collimator at said spatially optimized distribution set of station points or control points, wherein when at least two said apertures have a same gantry angle, said volumetric modulation arc therapy system operates said gantry rotation to stop at a gantry angle and operates delivery of radiotherapy doses to each said aperture one by one, wherein said volumetric modulation arc therapy system operates to not apply a radiotherapy dose when each said aperture is transitioning to a next aperture at the same gantry angle.

5. The method of radiation therapy planning and delivery of claim 1, wherein a delivery plan, used by said volumetric modulation arc therapy system, is capable of re-optimizing a segment shape and said beam weight of said spatially optimized distribution set of station points or control points.

6. The method of radiation therapy planning and delivery of claim 1, wherein a delivery plan, used by said volumetric modulation arc therapy system, comprises a step-and-shoot delivery operation or a continuous arc delivery operation.

7. A method of radiation therapy planning and delivery, comprising:
   a. pre-selecting or optimizing a number of non-uniform station points or control points from a spatially optimized distribution set of station points or control points, using a volumetric modulation arc therapy system, wherein a gantry is automatically positioned according to said pre-selected or optimized number of non-uniform station points or control points;
   b. simultaneously optimizing a shape or a weight of a field corresponding to each said pre-selected or optimized number of non-uniform station points or control points in a set of non-uniform control points with a spatial distribution of said control points, using said volumetric modulation arc therapy system; and
   c. moving said gantry and selecting a different set of non-uniform spatially optimized distribution of station points or control points at different gantry angles, using said volumetric modulation arc therapy system, wherein an optimization algorithm is provided to directly optimize an angular distribution and a spatial distribution of said different set of non-uniform spatially optimized distribution of station points or control points for positioning said gantry.

* * * * *